United States Patent [19]

Cialkowski et al.

[11] Patent Number: 5,346,593
[45] Date of Patent: Sep. 13, 1994

[54] INTERMEDIATE REBOILER FOR A METHANOL PLANT

[75] Inventors: Edward J. Cialkowski, Houston; Thomas P. Ognisty, The Woodlands, both of Tex.

[73] Assignee: The M. W. Kellogg Company, Houston, Tex.

[21] Appl. No.: 79,063

[22] Filed: Jun. 18, 1993

[51] Int. Cl.$^5$ .............................................. B01D 3/14
[52] U.S. Cl. ........................................ 203/18; 202/154; 202/155; 202/235; 203/25; 203/27; 203/78; 203/99; 203/DIG. 9; 203/DIG. 8; 203/DIG. 19; 203/DIG. 23; 568/913
[58] Field of Search ............... 203/18, 71, 99, 78, 203/DIG. 13, DIG. 9, DIG. 19, DIG. 23, 23, 25, 27, DIG. 8; 568/913; 202/154, 155, 176, 235; 435/157

[56] References Cited

U.S. PATENT DOCUMENTS

| | | | |
|---|---|---|---|
| 2,194,851 | 3/1940 | Guinot | 202/204 |
| 2,549,290 | 4/1951 | Congdon et al. | 203/DIG. 23 |
| 2,595,805 | 5/1952 | Morrell et al. | 203/82 |
| 3,239,435 | 3/1966 | Conpeiller et al. | 203/DIG. 23 |
| 4,013,521 | 3/1977 | Scott | 203/DIG. 19 |
| 4,210,495 | 7/1980 | Pinto | 203/DIG. 19 |
| 4,246,073 | 1/1981 | Umeda et al. | 203/25 |
| 4,592,806 | 6/1986 | Ilgner et al. | 203/DIG. 23 |
| 4,678,543 | 7/1987 | Houben et al. | 203/DIG. 13 |
| 4,744,869 | 5/1988 | Saito et al. | 203/DIG. 13 |
| 4,824,527 | 4/1989 | Erickson | 203/80 |

OTHER PUBLICATIONS

Ognisty, 1993 A.L.Ch.E. Spring National Meeting, Paper No. 21a, Mar. 30, 1993.
Kaibel et al., *Gas Separation and Purification*, vol. 4, Jun. 1990, pp. 109–114.
Kaibel, *International Chemical Engineering*, vol. 32, No. 4, Oct. 1992, pp. 631–641.

*Primary Examiner*—Virginia Manoharan
*Attorney, Agent, or Firm*—John P. Ward

[57] ABSTRACT

A methanol refining column and method using an intermediate reboiler. Use of the intermediate reboiler reduces methanol production energy requirements. A side stream at or near a fusel oil takeoff point is heated in an intermediate reboiler by a low temperature heating medium (relative to a bottoms reboiler) and returned to the column at or near the fusel oil take-off tray. The take-off tray is operated at 85°–110° C., and 70–90 percent of the reboiler duty is supplied through the intermediate reboiler. The remaining heat load is supplied by a bottoms steam reboiler.

13 Claims, 3 Drawing Sheets

INTERMEDIATE REBOILER FOR A METHANOL PLANT

FIELD OF THE INVENTION

The present invention relates to a methanol plant, and in particular to an energy-efficient methanol purification column having an intermediate reboiler.

BACKGROUND OF THE INVENTION

Efforts to reduce manufacturing costs of chemical products are on-going with particular attention directed to reducing energy costs by implementing heat integration design, that is, the process-wide pairing of heat-releasing streams with heat-accepting streams. In addition, energy usage has been lowered by the adoption of more thermodynamically efficient design of unit processes such as distillation, heat exchange, and the like.

Distillation, although energy intensive, is a very common in the separation technique chemical and petrochemical industries. Distillation processes consume on the order of 95 percent of the energy used for all separation processes. Heretofore, most distillation designs have not been very good at determining thermodynamic efficiency due to past difficulty in evaluating the internal dynamics.

As is well known, a reversible process is most efficient from a thermodynamic perspective. Insofar as a process deviates from the reversible ideal, more energy is required than the theoretical minimum. The difference between the actual work (energy) which a process requires and its reversible work is defined as lost work. By analyzing a process for irreversible elements, it is possible to determine improvements which can increase efficiency and reduce energy consumption. A general background discussion of some thermodynamic concepts as applied to distillation columns is presented in Ognisty, "Thermodynamic Analysis of Distillation Columns," Paper No. 21a, 1993 A.I.Ch.E. Spring National Meeting, Mar. 30, 1993, incorporated herein by reference.

Kaibel, G. et al., *Gas Separation and Processing*, Vol. 4, No. 2, June 1990, pp. 109-114; and Kaibel, G., *International Chemical Engineering*, Vol. 32, No. 4, October 1992, pp. 631-641; describe analysis of distillation systems to improve thermodynamic efficiency for reduction of energy usage.

In a distillation process, heat is converted into work, namely, the separation of one or more chemical components from a mixture thereof. Areas of lost work include fluid flow momentum losses (pressure drop) and the presence of driving forces which are at great disequilibrium. Examples of these driving forces include heat transfer between fluids having different temperatures, such as mixing fluids at different temperatures, and mass transfer between streams which are not at equilibrium, such as mixing streams having different component concentrations. Therefore, a key to greater distillation efficiency is to stay as close to equilibrium conditions as is economically feasible by keeping driving forces small and minimizing pressure drop.

In a practical sense, areas of excessive driving forces (disequilibrium) in the column can result in lost work, defined as that portion of the total work which is necessary to overcome thermodynamic inefficiency. It would, therefore, be beneficial to enhance the thermodynamic efficiency of a methanol distillation unit, and where significant amounts of heat can be added or removed at temperature levels significantly different than the available steam, cooling water and other utilities, to implement heat integration in the column to reduce the amount of utilities required for the distillation. Process heat integration would use heat efficiently and reduce the amount of utilities the plant is required to generate for operation. Reducing steam consumption would, in turn, minimize the amount of oil, natural gas or coal used to generate steam. Reducing cooling water rates would similarly minimize makeup water rates and cleanup requirements. The amount of chemical and biological treatment of boiler feed water is directly related to total steam demand. Not only would efficient energy use reduce the costs of operating a distillation column, but would also minimize the waste involved with producing and maintaining utilities.

SUMMARY OF THE INVENTION

This invention is directed to use of an intermediate reboiler, preferably at or near a fusel oil take-off point, in a methanol refining column to enhance overall thermodynamic efficiency. Use of the intermediate reboiler shifts a major portion of reboil heat to a lower temperature heating medium, thus lowering utilities demand. Furthermore, by matching the heat requirement of the intermediate reboiler to available waste heat in a process stream, heat integration can be implemented for even greater savings which can become multiplied when factors other than simple fuel reduction are taken into account. Heat integration can also reduce cooling water circulation and makeup, boiler water treatment, waste water cleanup, etc.

Broadly, the present invention provides a methanol plant having a generally conventional reforming unit for reacting steam and hydrocarbon gas feed to produce a synthesis gas; a heat recovery zone for cooling and recovering heat from the synthesis gas; a condensate separation zone for disengaging process condensate from the synthesis gas; a syngas compression zone for compressing the synthesis gas; a methanol synthesis zone for synthesizing methanol from the compressed synthesis gas; and a distillation zone for refining the synthesized methanol.

In a preferred embodiment, the methanol synthesis effluent is purified in a methanol refining column heated using an intermediate reboiler. The intermediate reboiler is operated adjacent a take-off zone of the fusel oil fraction and preferably has an operating temperature between about 85° C. and about 110° C. The fusel oil fraction is preferably withdrawn from a feed stream to the intermediate reboiler.

In a further embodiment, the present invention provides a methanol refining column comprising an upright vessel containing vapor/liquid contacting elements disposed between upper and lower ends thereof; an overhead condenser in fluid communication with the vessel adjacent to the upper end thereof; an optional pasteurizing section disposed in the upper end of the vessel; a methanol product outlet adjacent the upper end, preferably disposed below the pasteurizing section; a methanol enriching section disposed between the methanol product outlet and a mid-column feed inlet; a methanol stripping section disposed between the feed inlet and a fusel oil take-off zone; a methanol and fusel oil stripping section disposed below the fusel oil take-off zone; a bottoms reboiler in fluid communication with the vessel adjacent the lower end thereof; a bottoms outlet adjacent the lower end of the vessel; and an intermediate reboiler for supplying heated fluid to the vessel above the bottoms reboiler and adjacent the fusel oil take-off zone. The column can include a feed from the fusel oil take-off zone to the intermediate reboiler and a return line for heated liquid and vapor from the intermediate reboiler to the fusel oil rectifying section adjacent the fusel oil take-off zone. Preferably, a fusel oil stream is taken as a side-stream from the intermediate reboiler feed stream. The intermediate reboiler is preferably adapted to supply the heated fluid at a temperature of from about 85° C. to about 110° C.

In another embodiment, the present invention provides a method for refining methanol from an aqueous stream containing heavier organic contaminants. The method includes the steps of (a) feeding the aqueous methanol stream to an inlet zone of a refining column, below an upper rectifying section and above a lower stripping section; (b) refluxing condensate overhead; (c) recovering a high purity methanol product overhead; (d) recovering a fusel oil stream from a fusel oil take-off zone in the stripping section of the column; (e) heating the column adjacent the fusel oil take-off zone with an intermediate reboiler, preferably using a first, relatively low temperature heating medium; (f) heating the stripping section below the intermediate reboiler with a bottoms reboiler, preferably using a second, relatively high temperature heating medium; (g) withdrawing an aqueous bottoms product. As one option, the method can also include feeding a crude methanol stream to a topping column, recovering the components less volatile than methanol overhead from the topping column, recovering a bottoms product from the topping column which is essentially free of the volatile components and using the topping column bottoms product as the aqueous methanol stream fed to the refining column inlet zone in step (a). Preferably, the method includes the step of operating a pasteurization zone disposed above a methanol take-off zone for the overhead product recovery step (c). Preferably, the intermediate reboiler heating step includes recirculating fusel oil from the fusel oil take-off zone, through the intermediate reboiler, and back to the fusel oil take-off zone. The fusel oil recovery step (d) preferably comprises taking off a side stream from the fusel oil circulated to the intermediate reboiler. The fusel oil take-off zone is preferably operated at a temperature of from about 85° C. to about 110° C. The low temperature heating step (e) preferably supplies from about 70 to about 90% of the total heat supplied to the refining column. The low temperature heating medium in step (e) preferably is a process stream at a temperature lower than the high temperature heating medium in step (f). The high temperature medium in step (f) preferably comprises steam.

DETAILED DESCRIPTION OF THE INVENTION

Figure 1:
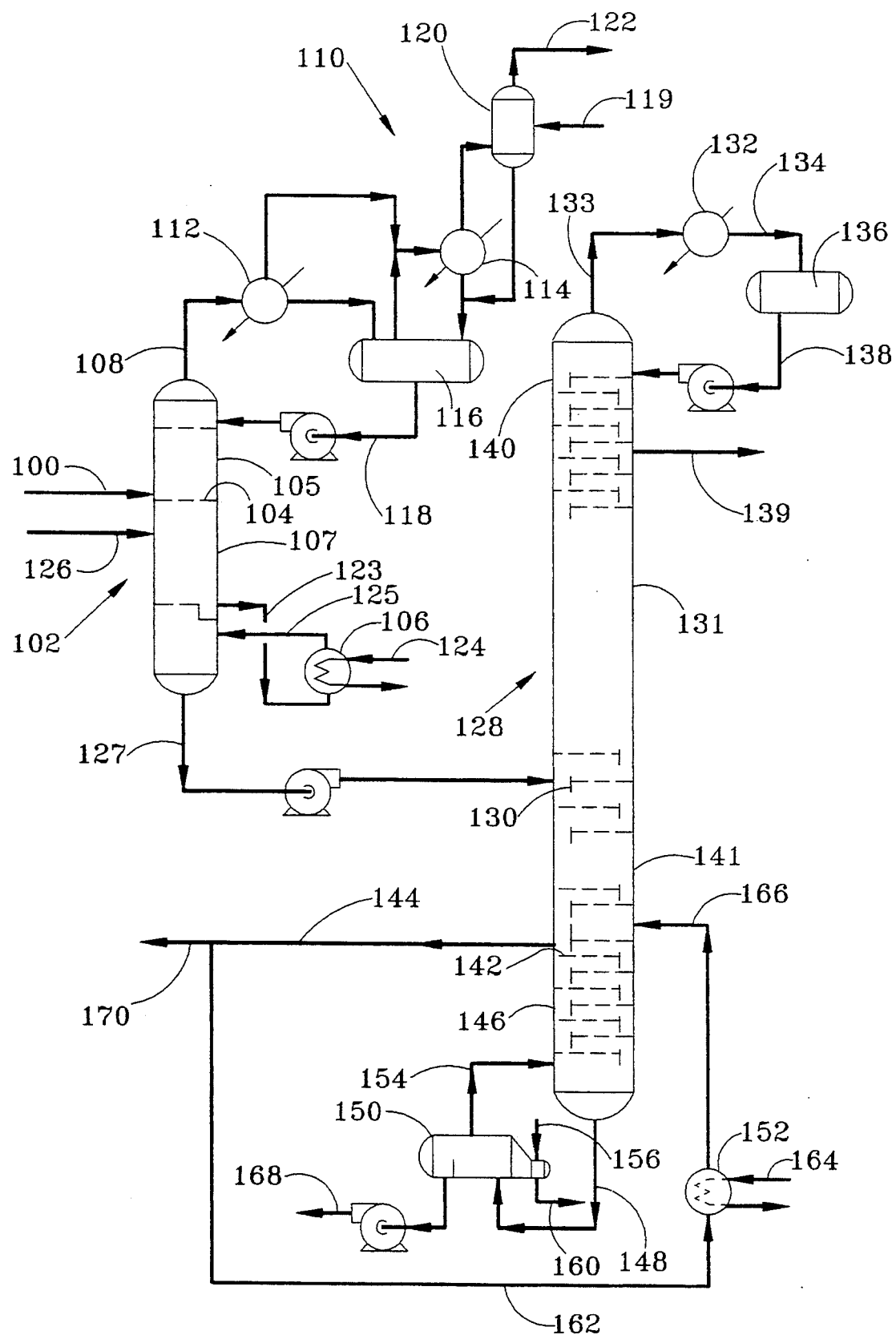
FIG. 1 is a schematic process flow diagram of a methanol distillation zone of the present methanol process showing an intermediate reboiler adjacent a fusel oil take-off tray of a methanol refining column.

In a methanol synthesis plant, the thermodynamic efficiency of a methanol refining column is enhanced using an intermediate reboiler without requiring an excessive number of additional stages to maintain the desired product purity. As an additional benefit, the present intermediate reboiler can be installed to coincide with a fusel oil sidedraw tray, improving the economics of the modification since fusel oil take-off is a standard requirement for the column.

In a catalytic methanol process, a hydrocarbon such as methane is reformed with steam to form $H_2$, CO and $CO_2$ comprising a methanol synthesis gas. The methanol synthesis gas from the reforming zone is directed to a waste heat recovery section wherein sensible and condensing heat of the gas is used to perform a variety of heating duties such as, for example, heating boiler feed water, vaporizing crude methanol, and the like. Since the synthesis gas contains excess steam, this steam becomes condensed and is removed in a process condensate separation stage. The cooled methanol synthesis gas is then compressed to a suitable methanol synthesis pressure, typically from about 6.2 to about 10.3 MPa (gauge) (900–1500 psig). (As used herein, all specified pressures are absolute unless gauge pressure is indicated.) The compressed methanol synthesis gas is conventionally introduced to a methanol synthesis unit wherein methanol is produced in the presence of a conventional copper catalyst, for example, at a temperature of about 210° C. to about 270° C. (410° F.–520° F.).

As is well known in the art, conversion to methanol is incomplete. Effluent from the methanol synthesis unit contains crude methanol, higher molecular weight by-products and unreacted methanol synthesis gas. The effluent is conventionally cooled to condense the methanol formed and uncondensed methanol synthesis gas is recycled. A portion of the unreacted synthesis gas is withdrawn as a purge in order to avoid accumulation of methane, nitrogen, and other inert substances, as well as excess hydrogen. The hydrogen in the purge gas can be used as a raw material in other synthesis reactions, such as ammonia synthesis, or as a fuel.

Methanol produced in the methanol synthesis unit can, and usually does, contain effluent products from the reforming zone and impurities formed by the methanol synthesis catalyst. Impurities in crude methanol are typically grouped in terms of relative volatility in comparison to methanol. More volatile or lighter components can include dissolved synthesis gas, methyl formate, acetone, trimethylamine, $C_{5-7}$ paraffins, and the like. Light components are conventionally distilled from crude methanol in a first or topping column.

Less volatile or heavier components include ethanol, i-propanol, n-propanol, i-butanol, n-butanol, n-pentanol, n-hexanol, $C_{9+}$ paraffins, water, and the like. Heavy components are distilled from crude methanol in a second or refining column. A refined methanol stream is recovered overhead. A distillation bottoms product comprising primarily water is also produced. The impurities formed are separated as a fusel oil fraction. Fusel oil, comprising primarily aqueous methanol (approximately 30–40 percent by weight) with a small amount of ethanol and other heavier components, is typically burned along with other fuels to heat the reforming furnace, but can also be stripped or evaporated for recycle of the organic components therein to the steam and/or hydrocarbon feed to the reforming zone.

As is well known, the key components for design of the methanol distillation unit are acetone in the topping column and ethanol in the refining column. To a large extent, distillation design parameters, including reflux ratio and number of stages, are determined by the concentration of these key impurities in the crude methanol feed and the desired purity requirements of the methanol product. Of the impurities in the crude methanol, ethanol is usually present in a greater concentration than the other organic impurities. Largely because of the methanol/ethanol separation requirement, the refining column generally comprises 80–90 percent of the energy requirements for methanol distillation. It has been determined that heat supplied by an intermediate reboiler generates sufficient methanol-rich vapor in the refining column to separate ethanol from methanol at a desired product purity level. The intermediate reboiler is preferably employed adjacent a take-off zone for the fusel oil fraction, i.e. where the ethanol concentration in the column is usually at its highest level. The present refining column significantly reduces the quality of energy required for the distillation unit, reducing steam heating requirements and allowing the use of a lower temperature heating medium, such as another process stream available at a lower temperature.

It is a primary requirement that the methanol refining column must be heated sufficiently to effect separation of methanol in a vapor phase from ethanol in a liquid phase. The methanol/ethanol separation occurs primarily in the rectifying section of the column. The methanol/ethanol separation is more difficult than the methanol/water separation, and governs the required heat load and flows through the column.

In the prior art methanol refining columns, all of the heat is supplied at the bottoms reboiler to generate essentially pure steam. As the water vapor passes up the column from the reboiler, it condenses to transfer heat to the methanol-rich phase. In contrast, the intermediate reboiler of the present invention supplies the portion of the heat required for the methanol-ethanol separation directly where it is needed, i.e. where the methanol/ethanol separation occurs. Because of the narrower boiling point difference between methanol (64.5° C.) and ethanol (78.3° C.), the total heat load of the methanol/ethanol separation is much greater than the classic methanol/water distillation, and the improved efficiency obtained by the intermediate reboiler placement in the present invention has a much greater practical significance.

Another characteristic aspect of the present invention is that the use of the intermediate reboiler does not add significantly to the number of equilibrium stages needed in the refining column. Since relatively large amounts of heat are transferred from vapor to liquid in a relatively few theoretical stages adjacent the intermediate reboiler, the presence of the intermediate reboiler does not require more than one additional theoretical equilibrium stage. In contrast, the use of the intermediate reboiler in many systems results in a mass transfer pinch which may require too many additional equilibrium stages, and consequently too much additional column height to be of practical application, Another beneficial characteristic of this invention is that the intermediate reboiler can be placed to coincide with the fusel oil side draw tray. Since a side tray is conventionally incorporated into the column design anyway, for fusel oil removal, additional costs can be saved by using the side draw tray to feed the intermediate reboiler, and withdrawing the fusel oil product stream as a side stream from the intermediate reboiler feed.

Referring to FIG. 1, crude methanol from the methanol synthesis unit (not shown) is initially directed in a line 100 to a topping distillation column 102 at an intermediate feed tray 104 roughly two-thirds the distance up the column 102 from a reboiler 106. The topping column 102 comprises a light end rectifying zone 105 above the feed tray 104 and a light end, particularly acetone, stripping zone 107 below the feed tray 104. Methanol and lighter vapor components are directed through an overhead line 108 to a divided condenser zone 110 to provide reflux liquid to the column 102.

The condenser zone 110 preferably includes first and second condensers 112 and 114, respectively, with the second condenser 114 operating at a temperature 10°–15° C. lower than the first condenser 112. Liquid methanol condensed by the first condenser 112 is fed to a reflux drum 116. The condensed methanol in the drum 116 is refluxed to the column 102 through line 118. The remaining vapor is directed to the second condenser 114 wherein an additional portion of the overhead methanol is condensed and fed to the drum 116. Vapor from the second condenser 114 is preferably scrubbed by water fed through line 119 to scrubber 120 wherein a further portion of the methanol is removed. Vapor from the scrubber 120 comprising synthesis gas and other volatile components is generally directed to a plant fuel system or other processing through line 122. Use of partial condensers 112 and 114 reduces the reboiler load by avoiding subcooling of the entire overhead reflux stream.

Feed to the reboiler 106 is withdrawn from the column 102 through line 123 adjacent a lower end of the stripping zone 107. Heat exchange is provided with a hot process fluid in line 124, although steam and/or hot water could also be suitably used for this purpose. The heated fluid, partially or completely vaporized, is returned to the column 102 through line 125.

If desired to maintain alkaline operating conditions, an aqueous solution of about 1 percent by weight caustic can be added to the topping column 102 through line 126. Maintaining a pH above 7 mitigates the potential for corrosion in process equipment and allows the use of relatively inexpensive materials of construction, such as carbon steel. The topping column 102 generally operates at a pressure slightly above atmospheric pressure on the order of 0.03–0.35 MPa(gauge) (about 5–50 psig).

Methanol, having a substantially reduced concentration of acetone and other light components, is removed as a bottoms product in line 127. Typically, acetone concentration in a refined methanol product (Grade AA) should be less than about 20 ppm by weight. The bottoms from the topping column 102 comprise primarily aqueous methanol and heavier impurities and are directed through line 127 to the refining column 128. Feed tray 130 is preferably about two-thirds down the height of the column 128, below condenser 132. The feed stream can be admitted to the column at any of a plurality of generally adjacent feed trays, as desired.

The refining column 128 includes a methanol enriching zone 131 above the feed tray 130. In the enriching zone 131, the methanol concentration is increased so that vapor removed overhead in line 133 is essentially pure methanol and the condenser 132 operates isothermally to supply reflux liquid to the column 128. Light methanol from the condenser 132 passes through line 134 into a reflux drum 136 for reflux back to the refining column 128 through line 138. The methanol product, however, is preferably withdrawn slightly down (about 3–10 percent) from the top to enable the uppermost trays to be used as a pasteurization section 140. Thus, any light end which manages to break through from the topping column 102 can be vented from the reflux drum 136. The high grade methanol product is directed through line 139 to a storage facility or to another manufacturing process. If paraffins (usually $C_9$–$C_{10}$ in the molecular weight range of 130–140) exceed desired content in the methanol production stream 139, a small purge stream (not shown) can be taken off at an intermediate point in the refining column 128.

The refining column 128 also includes a methanol stripping section 141 between the feed tray 130 and a fusel oil take-off zone adjacent tray 142. In the methanol stripping section 141, methanol concentration is reduced and heavy end impurities are enriched. A fusel oil fraction is withdrawn from the tray 142 through line 144. Although only one fusel oil take-off tray is shown, depending on process parameters and column design, a plurality of generally adjacent fusel oil take-off trays can be employed in the fusel oil take-off zone. Below the fusel oil take-off tray 142, the refining column 128 comprises a fusel oil stripping section 141 wherein the concentration of the organic components is sharply reduced. A bottoms stream comprising essentially water is removed from the refining column 128 through line 148.

The refining column 128 has first and second reboilers 150, 152 in fluid communication with the column 128 for heating the column. While any type of reboiler can be used, the first reboiler 150 is preferably a steam reboiler and the second (intermediate) reboiler 152 is preferably a cross-exchanger with a hot process stream 164, as shown in FIG. 1. The feed to the first reboiler 150 is preferably removed from the fusel oil stripping zone 146 through line 148 adjacent the bottom thereof. The first reboiler 150 partially vaporizes the reboiler feed by heat exchange, preferably with plant steam. The vapor is returned to the column 128 through line 154. Steam is supplied to the steam reboiler 150 through line 156 and condensate is removed from the steam reboiler 150 in line 160. A net bottoms stream from the methanol distillation column is directed through line 168 for disposal or further treatment and reuse in the process as desired.

An intermediate reboiler feed adjacent the fusel oil take-off tray 142 can be removed from the methanol stripping zone 141 through line 144 and vaporized in the second reboiler 152 by heat exchange with the hot process stream 164. The heated fluid, usually at least partially vaporized, is returned to the tray 142 via line 166. In a preferred arrangement, the relatively small fusel oil stream is withdrawn from the intermediate reboiler take-off line 144 as a side stream and directed through line 170 for further processing or disposal as mentioned above. The bulk of the take-off stream remaining after fusel oil withdrawal is directed to the intermediate reboiler 152 through line 162. The heated fluid from the reboiler 152 is returned to the refining column 128 through line 166 adjacent tray 142. The intermediate reboil fraction is preferably removed from a tray (or trays) having an operating temperature between about 85° C. and 110° C. and corresponding to the zone of maximum heavy end concentration, i.e., the fusel oil take-off point(s).

The intermediate reboiler 152 preferably supplies from about 70 to about 90 percent of the total reboiler duty required by the column 129. The refining column 128 generally operates at a pressure slightly above atmospheric pressure on the order of 0.03–0.35 MPa (gauge) (about 5–50 psig).

Use of an intermediate reboiler adjacent a fusel oil withdrawal point can improve the energy efficiency of the distillation column by shifting reboiler heat duty from the bottom of the column to an intermediate tray with a lower operating temperature. Thus, heat can be directly transferred to the point of the separation process where it is required using lower level plant steam and/or process waste heat as a heating medium.

Figure 3:
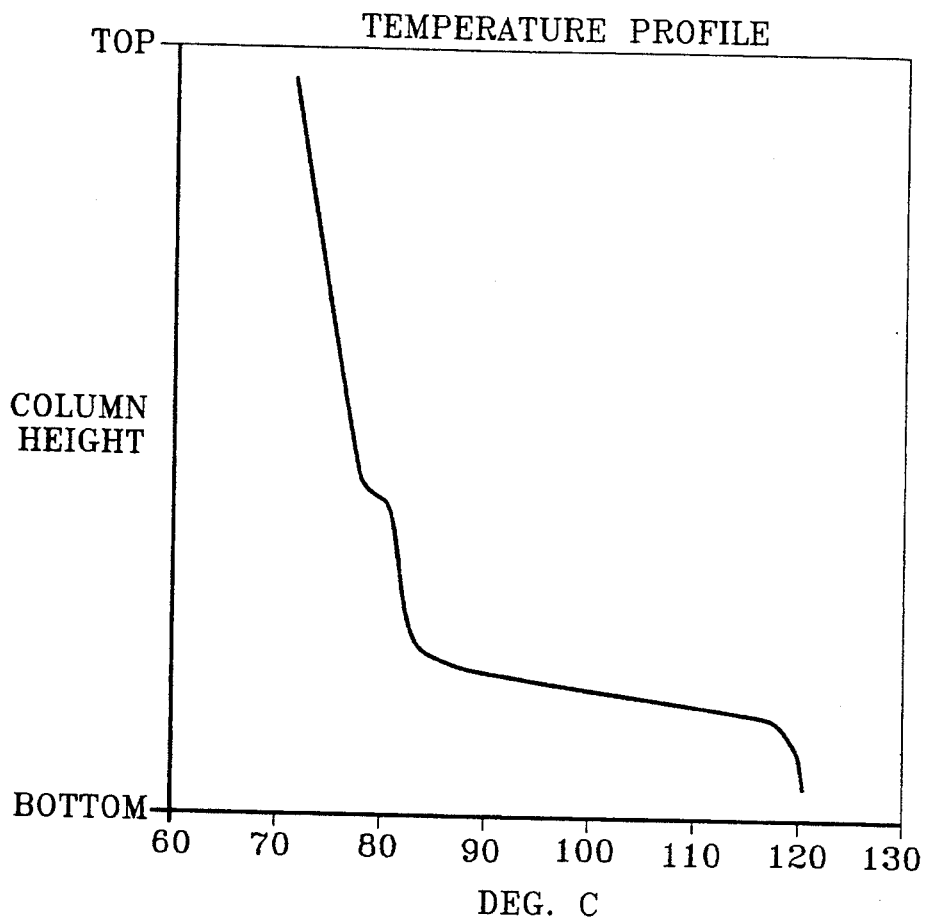
FIG. 3 is a graph of the column temperature profile versus column height for the same methanol refining column as in FIGS. 1 and 2.
Figure 4:
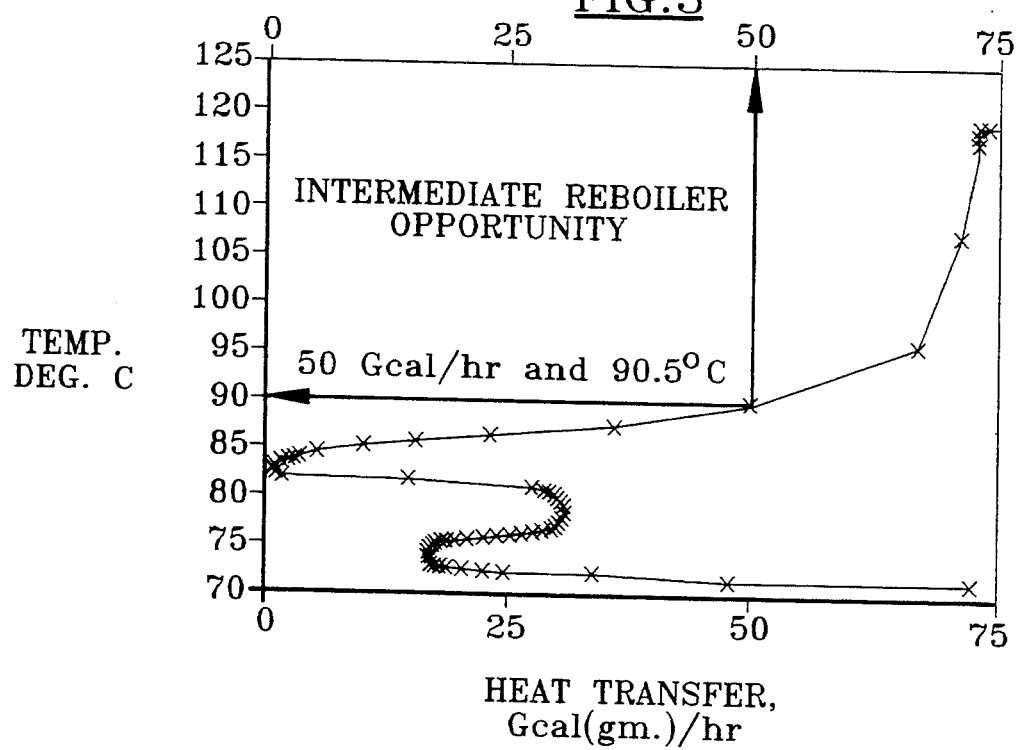
FIG. 4 is a graph of stage temperature versus heat transfer (grand composite curve (GCC)) for the methanol refining column of FIGS. 1–3 representing the amount of heat duty needed at a particular distillation stage and temperature level.

The fusel oil withdrawal or take-off point (the location of greatest impurity concentration) can be approximately 7 to 15 percent of the column height up from the bottom. This point also roughly coincides with the location at which the bulk separation of methanol and water is effected (i.e., diverging concentration profile curves) and consequently the heat demand point. Referring to FIG. 3, the column operating temperature at the fusel oil take-off point, as well as the intermediate reboiler take-off point, is generally between about 85° C. and about 110° C. For example, of the approximately 75 Gcal/hr required to heat the column, 50 Gcal/hr can be supplied by the intermediate reboiler at 90.5° C., as illustrated in the GCC shown in FIG. 4.

The present invention is further illustrated by the following example.

EXAMPLE

Figure 2:
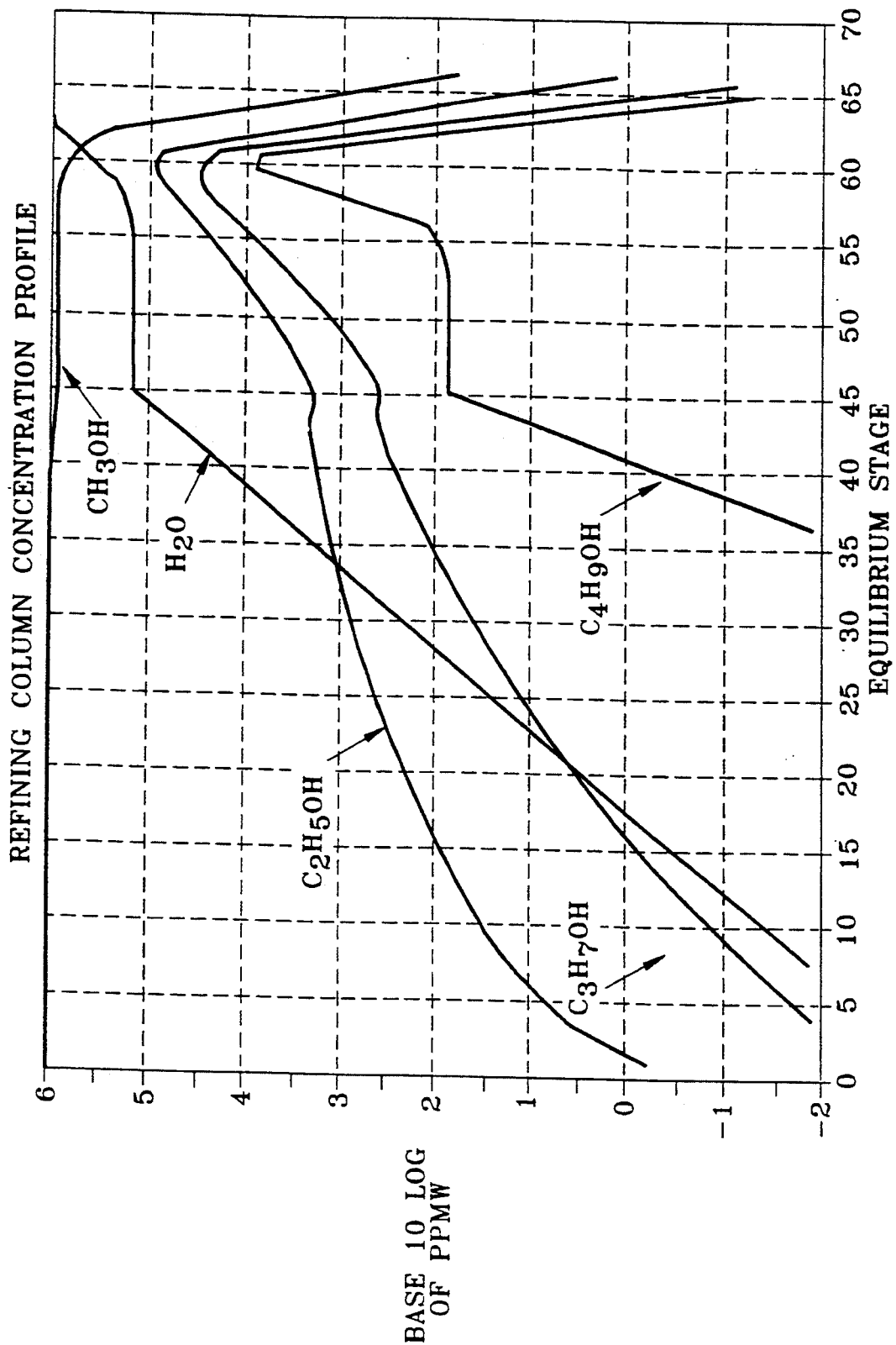
FIG. 2 is a graph of concentration profiles of the five primary components against the number of equilibrium stages of the methanol refining column of FIG. 1, plotting the log of the component equilibrium concentration in terms of ppm by weight wherein the condenser is the first stage and the primary reboiler is the last (sixty-sixth) stage.

The distillation zone of a methanol plant utilizing a topping distillation column and refining distillation column having an intermediate reboiler at the fusel oil take-off tray is simulated using a commercially available simulation program in accordance with techniques well known to those skilled in the art. The basis for the distillation column design is 2268 metric tons per day of US Grade AA methanol (less than 10 ppm(w) ethanol and 20 ppm(w) acetone). The feed condition of crude methanol is 0.2 MPa (gauge) pressure at 82.4° C. The intermediate reboiler is located at equilibrium stage 61 (8% above the bottom). Results of the refining column simulation in terms of the feed and outlet stream flowrates and compositions are given in Table 1. Results of the refining column simulation in terms of compositional profile of the five primary components at each equilibrium stage are graphically shown in FIG. 2. Stage temperature profile results are shown in FIG. 3.

TABLE 1

| | Stream Flow (kg mol/hr) | | | | |
|---|---|---|---|---|---|
| | Crude | Refining Column Material Balance | | | |
| Componen | Methanol Feed | Feed | Methanol Product | Fusel Oil | Bottoms |
| CO | 0.1 | 0.0 | 0.0 | 0.0 | 0.0 |
| $CH_3OH$ | 2988.2 | 2980.5 | 2949.4 | 31.1 | 0.0 |
| $H_2$ | 1.3 | 0.0 | 0.0 | 0.0 | 0.0 |

TABLE 1-continued

| Componen | Stream Flow (kg mol/hr) | | | | |
|---|---|---|---|---|---|
| | Crude Methanol Feed | Refining Column Material Balance | | | |
| | | Feed | Methanol Product | Fusel Oil | Bottoms |
| $CH_4$ | 2.3 | 0.0 | 0.0 | 0.0 | 0.0 |
| $CO_2$ | 17.4 | 0.0 | 0.0 | 0.0 | 0.0 |
| $H_2O$ | 1070.1 | 1174.1 | 0.0 | 84.2 | 1089.9 |
| $N_2$ | 0.0 | 0.0 | 0.0 | 0.0 | 0.0 |
| Light Ends[1] | 9.6 | <0.1 | 30 ppmw (max)[2] | 0.0 | 0.0 |
| Heavy Ends[1] | 10.5 | 10.5 | 10 ppmw (max)[3] | 10.5 | 0.0 |

[1]Taken as carbon-equivalent methanol impurities in the distillation train material balance (except for the product stream where Grade AA limits are indicated).
[2]30 ppmw acetone plus aldehydes.
[3]10 ppmw ethanol.

Additional simulation results determine that the condenser heat duty is −74.2 Gcal/hr with a top stage temperature of 71° C. The intermediate reboiler heat duty is 62.6 Gcal/hr with a stage temperature of 97° C. The bottoms reboiler heat duty is 12.6 Gcal/hr with a bottom stage temperature of 120° C.

In comparison to a conventional column having a single reboiler, 81 percent of the heat duty is supplied through the intermediate reboiler at a point in the distillation process having a lower operating temperature (97° C. instead of 120° C.). This lowers the heat level required by a heating medium and allows process waste heat, usually otherwise rejected to cooling water, to be utilized in the column. More process heat (11.25 Gcal/hr) is recovered in the distillation process with an almost equal magnitude of reduction in demand on the plant steam utility system. Based on a methanol plant with a 10.0 MPa high pressure steam system and using 0.4 MPa low pressure steam for the refining column reboil duty, the fuel credit for reducing low pressure steam demand is equal to 0.54 Gcal/hr of fuel per Gcal/hr of condensing duty. Based on this relationship, the reboil savings noted above for a 2268 metric ton plant is determined to be equivalent to 0.064 Gcal (0.25 MMBTU) per metric ton of methanol produced.

Moreover, these energy savings are obtained with no significant change in the capital costs between the use of the intermediate reboiler with a smaller steam reboiler versus the use of the steam reboiler alone.

The present method and apparatus are illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

We claim:

1. A methanol refining column, consisting essentially of:
    an upright vessel containing vapor-liquid contacting elements disposed between upper and lower ends thereof;
    an overhead condenser in fluid communication with the vessel adjacent the upper end thereof;
    a methanol product outlet disposed adjacent the upper end of the vessel;
    a methanol enriching section disposed between the methanol product outlet and a mid-column feed inlet;
    a methanol stripping section disposed between the feed inlet and a fusel oil take-off zone;
    a methanol and fusel oil stripping section disposed below the fusel oil take-off zone;
    a bottoms reboiler in fluid communication with the vessel adjacent the lower end thereof;
    a bottoms outlet adjacent the lower end of the vessel;
    an intermediate reboiler for heating the vessel above the bottoms reboiler and adjacent the fusel oil take-off zone; and
    a line from the fusel oil take-off zone to feed the intermediate reboiler, and a side-stream from the intermediate reboiler feed for fusel oil take-off.

2. The column of claim 1, including a pasteurizing section disposed in the upper end of the vessel.

3. The column of claim 1, including a return line for heated fluid from the intermediate reboiler to the fusel oil stripping section adjacent the fusel oil take-off zone.

4. The column of claim 1, wherein the intermediate reboiler is operated at a temperature of from about 85° C. to about 110° C.

5. A method for refining methanol from an aqueous stream containing heavier organic contaminants, consisting essentially of the steps of:
    (a) feeding the aqueous methanol stream to an inlet zone of a refining column below an upper rectifying section and above a lower stripping section;
    (b) refluxing condensate overhead;
    (c) recovering a refined methanol product overhead;
    (d) recovering a fusel oil stream from a fusel oil take-off zone in the stripping section;
    (e) heating the column adjacent the fusel oil take-off zone with an intermediate reboiler by recirculating fusel oil from the fusel oil take-off zone, through said intermediate reboiler, and back to said fusel oil take-off zone;
    (f) heating the stripping section below the intermediate reboiler with a bottoms reboiler using a heating medium; and
    (g) withdrawing an aqueous bottoms product.

6. The method of claim 5, further consisting essentially of the steps of: (h) feeding a crude methanol stream to a topping column; (i) recovering components less volatile than methanol overhead from the topping column; (j) recovering a bottoms product from the topping column essentially free of said volatile components; and (k) using the topping column bottoms product for said aqueous methanol stream feeding step (a) to the refining column inlet zone.

7. The method of claim 5, further consisting essentially of the step of: (1) operating a pasteurization zone disposed above a methanol take-off zone for said overhead product recovery step (c).

8. The method of claim 5, wherein said fusel oil recovery step (d) comprises taking off a side stream from the fusel oil circulated to the intermediate reboiler in step (e).

9. The method of claim 5, wherein the fusel oil take-off zone is operated at a temperature of from about 85° C. to about 110° C.

10. The method of claim 5, wherein the intermediate reboiler heating step (e) supplies from about 70 to about 90 percent of the total heat supplied in said heating steps.

11. The method of claim 5, wherein the first heating medium in heating step (e) has a temperature less than the temperature of the second heating medium in step (f).

12. The method of claim 5, wherein the heating medium in step (f) consisting essentially of steam.

13. A method for refining methanol from an aqueous stream containing heavier organic contaminants, consisting essentially of the steps of:

(a) feeding the aqueous methanol stream to an inlet zone of a refining column below an upper rectifying section and above a lower stripping section;

(b) refluxing condensate overhead;

(c) recovering a high purity methanol product overhead;

(d) feeding a stream to an intermediate reboiler from a fusel oil take-off zone having a temperature of from about 85° C. to about 110° C.;

(e) recovering a fusel oil product as a side-stream from the intermediate reboiler feed stream;

(f) heating fusel oil in the intermediate reboiler with a process stream in heat exchange therewith to supply from about 70 to about 90 percent of a heat load in the column;

(g) recirculating the heated fusel oil from step (f) to the fusel oil take-off zone;

(h) heating the refining column in a bottoms reboiler with steam having a temperature above about 120° C. and greater than the temperature of the hot process stream in step (f), to supply from about 10 to about 30 percent of the heat load to the column; and (i) withdrawing an aqueous bottoms product from the column.

* * * * *